(12) United States Patent  
Kloster

(10) Patent No.: US 8,863,344 B2  
(45) Date of Patent: Oct. 21, 2014

(54) MECHANICALLY DRIVEN RESONANT DRIVE POWER TOOTHBRUSH

(75) Inventor: Tyler G. Kloster, Snoqualmie, WA (US)

(73) Assignee: Koninklijke Philips N.V., Eindhoven (NL)

( * ) Notice: Subject to any disclaimer, the term of this patent is extended or adjusted under 35 U.S.C. 154(b) by 238 days.

(21) Appl. No.: 13/502,392

(22) PCT Filed: Oct. 15, 2010

(86) PCT No.: PCT/IB2010/054693

§ 371 (c)(1),
(2), (4) Date: Apr. 17, 2012

(87) PCT Pub. No.: WO2011/058466

PCT Pub. Date: May 19, 2011

(65) Prior Publication Data

US 2012/0216358 A1 Aug. 30, 2012

Related U.S. Application Data

(60) Provisional application No. 61/261,402, filed on Nov. 16, 2009.

(51) Int. Cl.
*A61C 17/32* (2006.01)
*A61C 17/34* (2006.01)
(52) U.S. Cl.
CPC .................................. *A61C 17/3481* (2013.01)
USPC ............................................. 15/22.2; 15/22.1

(58) Field of Classification Search
USPC .......................................... 15/167.1, 22.1–24
See application file for complete search history.

(56) References Cited

U.S. PATENT DOCUMENTS

| | | |
|---|---|---|
| 5,378,153 A | 1/1995 | Giuliani et al. |
| 6,140,723 A | 10/2000 | Matsui et al. |
| 6,833,639 B2 | 12/2004 | Lau et al. |
| 2008/0028547 A1 | 2/2008 | Miller et al. |
| 2008/0209650 A1 | 9/2008 | Brewer et al. |

FOREIGN PATENT DOCUMENTS

| | | |
|---|---|---|
| WO | 03092535 A2 | 11/2003 |
| WO | 2008001302 A2 | 1/2008 |
| WO | 2009113368 A1 | 9/2009 |

*Primary Examiner* — Shay Karls

(57) ABSTRACT

The power toothbrush includes a handle (12) and a workpiece assembly (18) which includes a brushhead (20) at a forward end thereof. The toothbrush further includes a drive assembly (14) which includes a DC motor (26) having a rotating output shaft (41) and a mounting assembly (28) for flexibly mounting the motor to the handle. The drive assembly includes a torsion spring member (64), an eccentric member (52), a coupling member (44) for connecting the rotating output shaft of the motor to the rear end of the eccentric and a hub member (62) forward of the eccentric, wherein the other end of the eccentric extends to and is mounted to the hub member. The torsion spring extends between the motor mount and the hub member. In operation, the rotating eccentric excites a desired resonant mode in the torsion spring, resulting in a sweeping back and forth action of the workpiece assembly and the brushhead.

14 Claims, 2 Drawing Sheets

MECHANICALLY DRIVEN RESONANT DRIVE POWER TOOTHBRUSH

This invention relates generally to power toothbrushes and more specifically concerns a drive train using a torsion spring system which is excited at or near its desired resonant mode to produce the cleansing action.

Torsion spring assemblies have been and are used to provide the driving action for the brush assemblies of some power toothbrushes. In one arrangement, the torsion spring is excited by an oscillating magnetic field to accomplish the desired brushhead action. However, such a magnetically actuated drive train requires a custom actuator which in turn requires a sinusoidal signal to create the required oscillating magnetic field. The actuator and the electronics necessary to produce the sinusoidal signal can be expensive and add complexity to the manufacture of the toothbrush.

Hence, it is desirable to have a torsion spring drive train which is inexpensive compared to magnetic actuation arrangements and which are reliable in operation and convenient to manufacture.

Accordingly, the power toothbrush, comprising: a handle; a workpiece assembly, including a brush arm and a brushhead at the end thereof; and a drive assembly, including a motor assembly, a torsion spring member for driving the workpiece assembly, and an assembly for mechanically exciting the torsion spring in a desired resonant mode, providing a sweeping, back and forth action of the brushhead.

Figure 1:
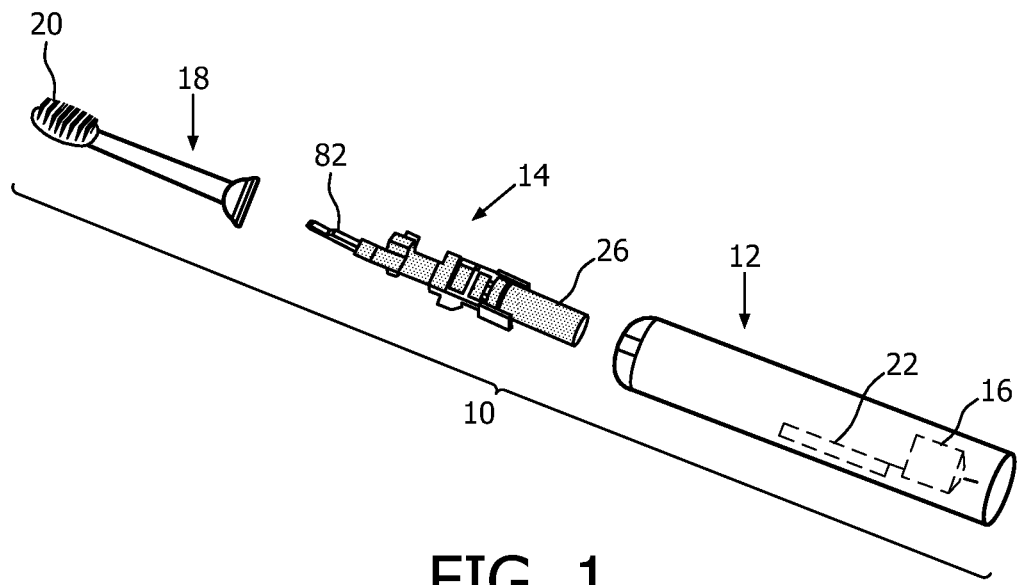
FIG. 1 is a partially exploded view of a power toothbrush with the drive train disclosed herein.

FIG. 1 shows a power toothbrush at 10. The power toothbrush 10 generally includes a handle 12, a drive train assembly 14, powered by a battery 16, and a brush arm assembly 18 with a brushhead 20 at the end thereof. The power toothbrush 10 is actuated by an on/off switch (not shown). A microprocessor 22 controls the operation of toothbrush 10.

Figure 2:
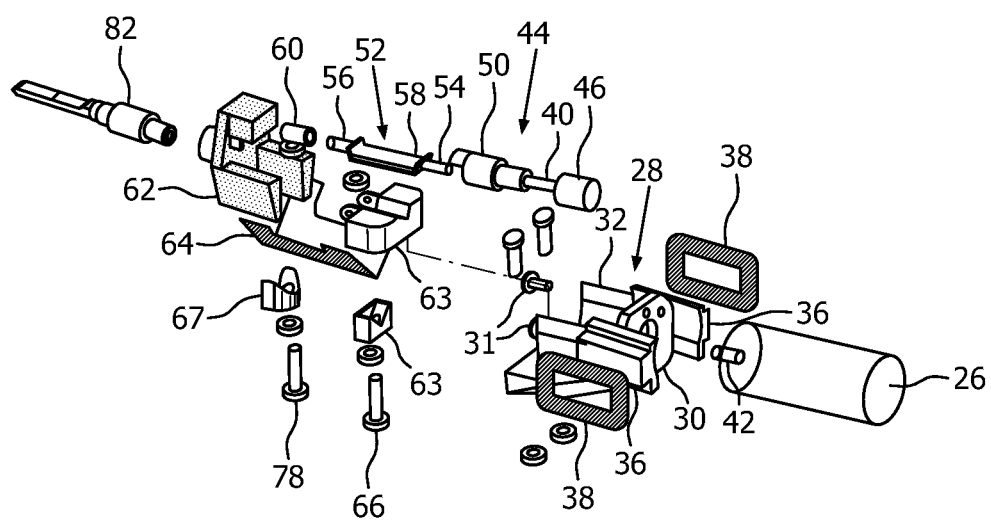
FIG. 2 is an exploded view of the drive train shown in FIG. 1.
Figure 3:
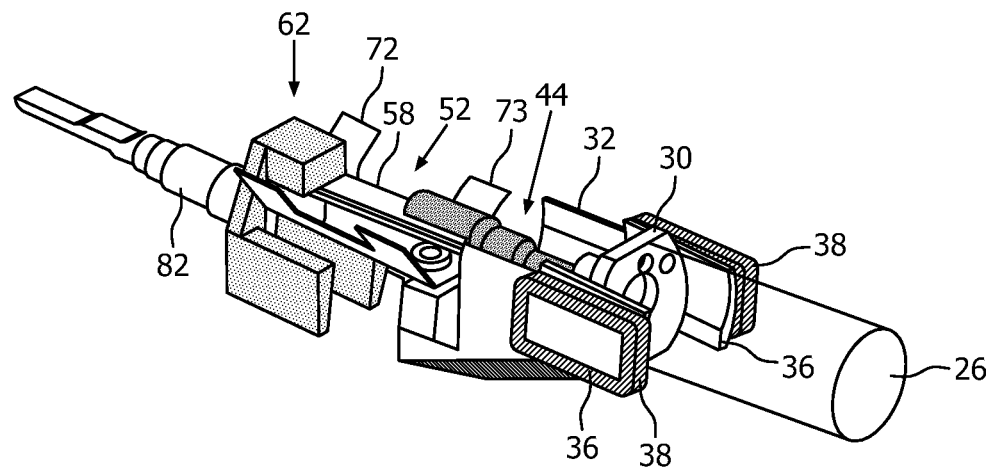
FIG. 3 is a perspective view of the drive train.

FIG. 2 is an exploded view of the drive train assembly 14, while FIG. 3 shows the drive train assembled. Drive train 14 includes a DC motor 26. In the embodiment shown, motor 26 is relatively high speed with a moderately low torque, 12,000 rpm to 16,800 rpm, with a torque in the range of 0.5 mNewton-meters to 1.5 mNewton-meters. The advantage of the DC motor is its low expense and relatively small size, both of which are important in a toothbrush. The speed and torque of the motor can, however, be varied.

Motor 26 is secured to a motor mount, shown generally at 28, and more specifically is connected to an end portion/ flange 30 of the motor mount, by means of screws 31, which extend through flange 30 into the forward end of the motor. The motor mount acts as a ground to the handle 12, although it is not rigidly fixed to the handle, as discussed in more detail below. In the embodiment shown, motor mount 28 is plastic, but could be made from other materials as well, such as metal. Motor mount 28 includes a half-cylindrical wall 32. It could include spaced rib members along its length for added strength. At the rear of the motor mount assembly 28 are two opposing wing members 36-36. Extending around the periphery of each wing member is an O-ring 38, which contacts the interior surface of the handle. The O-ring provides a flexible, elastic, i.e. non-rigid, connection between the motor mount and the handle, while still grounding the motor mount and the motor to the handle. This arrangement results in the absorption of some of the energy from the action of the spring portion of the drive train which is not necessary for operation of the drive train.

DC motor 26 includes an output shaft 42. Secured to and extending from output shaft 42 is an elastic coupling member 44. Coupling member 44 includes a rear or base portion 46 which is generally cylindrical, approximately 5 mm in diameter, and 6 mm long. This is followed by a smaller diameter (approximately 1.5 mm) portion 48. Extending from the forward end of smaller diameter portion 48 is an attachment portion 50 to which is connected an eccentric member 52. The eccentric member includes rod-like portions 54 and 56 which extend from opposing ends of a solid half-cylinder center portion 58. The center of mass of eccentric 52 is offset from the axis of rotation of the motor output shaft 42. Eccentric 52 can take various shapes, but must develop sufficient force as it spins to excite the spring portion of the drive train, as discussed below.

The forward rod-like portion 56 extends into a bushing portion 60 of a brush hub member 62. In the embodiment shown, brush hub 62 is made of a soft metal such as zinc, but it also could be plastic. The eccentric extends into the bushing 60 with a loose fit. A snug fit is undesirable for proper operation. The loose fit results in an easier rotation of the eccentric.

Also extending from motor mount 28 is a torsion spring 64. In the embodiment shown, torsion spring 64 is V-shaped, approximately 90° in the embodiment shown, but which could be between 50° and 120°. Other torsion spring members, such as a torsion bar or coil spring can be used, although they would typically require additional bearing support for resisting user loads and the undesired up/down forces from the eccentric. Torsion spring 64 extends from the motor mount to the lower edge of brush hub 62. The rear end of torsion spring 64 is connected to the forward end of motor mount 28 by a support assembly which includes a spring mount fitting 63. Screw 66 attaches the V-spring to the spring mount fitting 63. The spring mount fitting 63 is made of zinc and is attached to the motor mount by screw 65. Fitting 63 could, however, be part of an injection molded plastic motor mount. The other end of torsion spring 64 is captured to the lower edge of brush hub 62 by a similar fitting 67 and associated screw 78.

Figure 4:
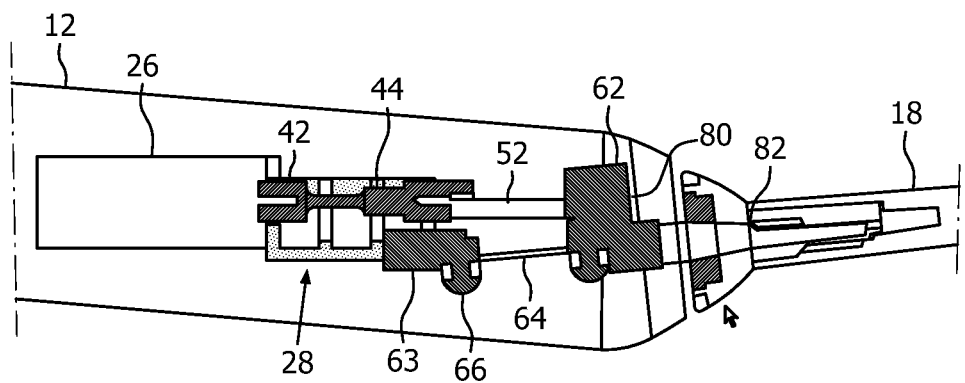
FIG. 4 is a cross-sectional view of the drive train in a power toothbrush.

The forward end of V-spring 64 is positioned below the forward end of the eccentric 52. This is shown most clearly in FIGS. 3 and 4. In the embodiment shown, V-spring 64 is between 20-60 mm in length, and has a spring rate which can vary between 0.6 Newton-meters per radian and 2 Newton-meters per radian. The V-spring is made of spring steel, approximately 0.3 mm thick in the embodiment shown, but the thickness could be in the range of 0.2-0.8 mm. The V-spring along each upper edge has a cutout portion 70 with two small ear-like protrusions 72, 73 at the forward and rear ends thereof. The cutout portion is approximately 6 mm deep. The cutout provides a gradual stiffness transition from the deforming portion of the V-spring to the rigid clamps at the ends thereof. This results in a more gradual, lower stress gradient in the spring.

Extending from the forward surface 80 of brush hub 62 (FIG. 4) near the lower end thereof is a brushhead drive shaft 82. Brush arm assembly 18 fits onto the brushhead drive shaft 82 in a removable fashion.

The distance between the axis of rotation of eccentric 52 and the axis of the brush arm assembly and the V-spring is referred to as the moment arm of the drive train. The larger the moment arm, the more torque produced by the eccentric as it spins. Generally, the moment arm should be as small as possible for a convenient size toothbrush, but must be large enough to produce the required torque necessary to excite the spring 30 as to produce effective cleansing action. A moment arm between 4-11 mm is typically sufficient to provide the necessary torque.

In operation, the spinning of the eccentric member 52 by action of the DC motor 26 at the correct frequency will excite the V-spring 64 in the desired resonant mode, in turn creating the desired motion for the brush arm assembly and the brushhead. In the embodiment shown, the resulting frequency of brushhead motion is between 200-280 Hz. The V-spring constrains the motion of the eccentric 52 to a sweeping alternating (bi-directional) motion. This is because the V-spring is compliant, i.e. softer, in torsion and stiffer in bending, i.e. it is amenable to a twisting action along its length while resisting a bending motion. Depending on the stiffness of the spring, the resonant frequency of the alternating (back and forth) motion of the brush arm assembly can be varied. With the above arrangement, the amplitude of the brushhead 20 will be 10° total, ±5° on either side of neutral, although the total amplitude could be up to 20°.

The amplitude can be controlled by the stiffness of the spring member, the mass and amount of eccentricity (distance off-center of the eccentric mass) of the eccentric, the frequency of operation of the article, the distance between the V-spring axis of rotation and the eccentric center of rotation and the rotation inertia of the rotating portion of the system. As discussed above, the V-spring which produces the sweeping motion is excited at its desired resonant mode mechanically by a DC motor and an eccentric. This arrangement provides a power toothbrush with reliable, effective motion at a relatively low cost.

Although a preferred embodiment has been disclosed for purposes of illustration, it should be understood that various changes and modifications and substitutions could be made in the preferred embodiment without departing from the spirit of the invention as defined by the claims which follow:

1. A power toothbrush, comprising:
   a handle;
   a workpiece assembly with a brushhead at the end thereof; and
   a drive assembly for driving the workpiece assembly, including a motor having a rotating output shaft, a mounting assembly for mounting the motor within the handle, a torsion spring member, an eccentric member, a coupling member for connecting the rotating output shaft of the motor and a rear end of the eccentric member, and a hub member, wherein the other end of the eccentric member extends to and is mounted at the hub member and wherein the torsion spring member extends between the mounting assembly for the motor and the hub member, wherein in operation, at a specific frequency, the rotating eccentric member excites a desired resonant mode in the torsion spring member, providing a sweeping back and forth action for the workpiece assembly and the brushhead.

2. The power toothbrush of claim 1, wherein the motor comprises a DC motor, operating at 12,000-16,000 rpm with a torque of 0.5 mNewton-meters to 1.5 mNewton-meters.

3. The power toothbrush of claim 1, wherein the torsion spring member comprises a V-spring, with an included angle of between 50° and 120°, a length in the range of 20-60 mm and a spring rate in the range of 0.5 Newton-meters and 2 Newton-meters.

4. The power toothbrush of claim 1, wherein a frequency of operation of the sweeping back and forth action is 200-280 Hz, and wherein an amplitude of the sweeping back and forth action of the brushhead is within the range of 7°-20°.

5. The power toothbrush of claim 1, wherein the eccentric is member comprises a solid half-cylinder.

6. The power toothbrush of claim 1, wherein the eccentric member is loosely mounted in a bushing which in turn is mounted in the hub member.

7. The power toothbrush of claim 1, further comprising elastic members positioned between the mounting assembly and the handle, providing a flexible, energy-absorbing connection therebetween.

8. The power toothbrush of claim 1, wherein a moment arm between (i) an axis of the eccentric member and (ii) a longitudinal axis of a brush arm of the workpiece assembly is within the range of 5-11 mm.

9. A power toothbrush, comprising:
   a handle;
   a workpiece assembly with a brushhead at the end thereof; and
   a drive assembly within the handle, wherein the drive assembly comprises a motor assembly, a torsion spring member for driving the workpiece assembly, and a spring exciting assembly, wherein the spring exciting assembly comprises an eccentric which rotates by action of a motor of the motor assembly for mechanically exciting the torsion spring member in a desired resonant mode, providing a sweeping back and forth action of the brushhead.

10. The power toothbrush of claim 9, wherein the motor is a DC motor having a rotating output shaft.

11. The power toothbrush of claim 10, wherein (i) a moment arm of the drive assembly between an axis of rotation of the eccentric and a longitudinal axis of a brush arm of the workpiece assembly and (ii) force from the eccentric rotating by action of the DC motor results in sufficient torque to excite the torsion spring member in a desired mode.

12. The power toothbrush of claim 9, wherein the motor is a DC motor, operating at 12,000-16,800 rpm with a torque of 0.5 mNewton-meters to 1.5 mNewton-meters.

13. The power toothbrush of claim 9, wherein a frequency of operation of the sweeping back and forth action is 200-280 Hz, and wherein an amplitude of the sweeping back and forth action of the brushhead is within the range of 7°-20°.

14. The power toothbrush of claim 9, wherein the motor is mounted in a motor mount and wherein the drive assembly further includes elastic members positioned between the motor mount and an interior surface of the handle, providing a flexible, energy-absorbing connection therebetween.

* * * * *